United States Patent [19]

Paltauf et al.

[11] Patent Number: 4,814,112
[45] Date of Patent: Mar. 21, 1989

[54] SINGLE-STAGE PROCESS FOR PREPARING MIXED-SUBSTITUTED 1,2-DIACYL-SN-CLYCERO-3-PHOSPHO-CHOLINES

[75] Inventors: Friedrich Paltauf; Albin Hermetter, both of Graz; Rudolf Franzmair, Linz, all of Austria

[73] Assignee: CL Pharma Aktiengesellschaft, Linz, Austria

[21] Appl. No.: 119,366

[22] Filed: Nov. 10, 1987

[30] Foreign Application Priority Data

Nov. 13, 1986 [DE] Fed. Rep. of Germany ....... 3638687

[51] Int. Cl.$^4$ ............................................... C07F 9/10
[52] U.S. Cl. .................... 260/403; 260/389; 548/112; 548/113
[58] Field of Search ............... 260/403, 389; 548/112, 548/113

[56] References Cited

U.S. PATENT DOCUMENTS 3,577,446  5/1971  Rakhit ................................. 260/403
4,622,180 11/1986  Paltauf et al. ...................... 260/389
4,710,579 12/1987  Nujima et al. ...................... 548/112
4,717,512  1/1988  Paltauf et al. ...................... 260/389

FOREIGN PATENT DOCUMENTS 0255798 12/1985  Japan ................................. 260/403
197804  10/1977  Netherlands ........................ 260/403

OTHER PUBLICATIONS

"The Nomenclature of Lipids", Biochem. J. 171 (1978), pp. 29–35.

Primary Examiner—Patrick P. Garvin
Assistant Examiner—Elizabeth D. Irzinski
Attorney, Agent, or Firm—Mark Dryer

[57] ABSTRACT

Single-stage process for preparing mixed-substituted enantiomerically pure 1,2-diacyl-sn-glycero-3-phosphocholines of general formula I

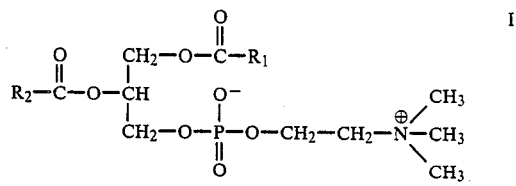

in which $R_1$ and $R_2$ are different and independently of each other denote a substituted or unsubstituted $C_1$ to $C_{24}$-alkyl or $C_3$ to $C_{24}$-alkenyl radical, by reacting 1-O-triphenylmethyl-2-acyl-sn-glycero-3-phosphocholine of the general formula

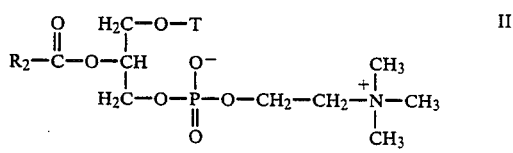

in which T denotes a substituted or unsubstituted triphenylmethyl group and $R_2$ is as defined above, with a reactive carboxylic acid derivative of the general formula

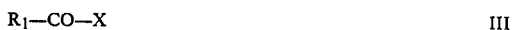

in which $R_1$ is as defined above and X denotes a carboxylic acid radical, a carbonic acid radical, a sulfonic acid radical or the radical of a fused or unfused five-membered heterocycle having at least two N atoms in the ring, in the presence of a protonic acid, of a Lewis acid or of adducts thereof with electron donors, and isolating the resulting compounds of the general formula I from the reaction mixture.

10 Claims, No Drawings

SINGLE-STAGE PROCESS FOR PREPARING MIXED-SUBSTITUTED 1,2-DIACYL-SN-CLYCERO-3-PHOSPHOCHOLINES

The present invention relates to a novel, singlestage process for preparing chemically defined enantiomerically pure 1,2-diacyl-sn-glycero-3-phosphocholines which are substituted in positions 1 and 2 of the glycerol independently of each other by different acyl radicals, from known intermediates.

U.S. Pat. No. 4,622,180 describes unsubstituted and substituted 1-O-triphenylmethyl-sn-glycero-3-phosphocholines as new intermediates for the synthesis of phosphatidylcholines. More particularly, these intermediates can be used to prepare in a simple manner mixed-substituted enantiomerically pure, 1,2-diacyl-sn-glycero-3-phosphocholines by first introducing in the free 2-position of the glycerol the desired acyl radical to form a 1-O-triphenylmethyl-2-acyl-sn-glycero-3-phosphocholine, detaching the protective 1-O-triphenylmethyl group to isolate a 2-acyl-sn-glycero-3-phosphocholine as a further intermediate and finally converting this intermediate in the last, separate process step into the desired end product by acylation in position 1 of the glycerol.

Although the process disclosed in U.S. Pat. No. 4,622,180 represents a substantial advance in the synthesis of mixed-substituted 1,2-diacyl-sn-glycero-3-phosphocholines and for the first time makes it possible to prepare this important class of compound in an economical and time-saving manner even on an industrial scale, it is an object of the present invention to simplify the process even further, specifically, having regard in particular to the use thereof in industry, to combine several process steps by not isolating or separating off individual intermediates.

We have found that this object is achieved by the present invention in an unexpectedly simple and effective manner in the form of a single-stage process whereby 1-O-triphenylmethyl-2-acyl-sn-glycero-3-phosphocholines can be coverted directly, in a single-vessel reaction, into mixed-substituted 1,2-diacyl-sn-glycero-3-phosphocholines.

The present invention accordingly provides a single-stage process for preparing mixed-substituted enantiomerically pure 1,2-diacyl-sn-glycero-3-phosphocholines of the general formula

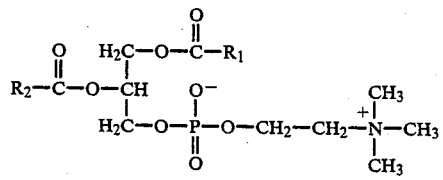

in which each of
$R_1$ and $R_2$ is different and independently of each other is a straight-chain or single or multiple branched unsbustituted $C_1$ to $C_{24}$-alkyl or or mono- or polyunsaturated $C_3$ to $C_{24}$-alkenyl group or a straight-chain or single or multiple branched monosubstituted or polysubstituted $C_1$ to $C_{24}$-alkyl or mono- or polyunsaturated $C_3$ to $C_{24}$-alkenyl group, wherein the substituent is chlorine, bromine, iodine, fluorine, or a $C_1$ to $C_4$-alkoxy group, which comprises reacting a 1-O-triphenylmethyl-2-acyl-sn-glycero-3-phosphocholine of the general formula

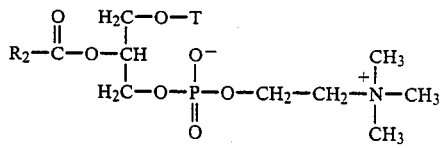

in which $R_2$ is as defined in formula I and T is an unsubstituted triphenylmethyl group or a triphenylmethyl group monosubstituted or polysubstituted on one, two or all phenyl groups, wherein the substituent is a straight-chain or branched $C_1$ to $C_6$-alkyl or $C_1$ to $C_6$-alkoxy group or chlorine, bromine, iodine or fluorine, with a reactive carboxylic acid derivative of the general formula $$R_1-CO-X \qquad \text{III}$$

in which
$R_1$ is as defined in formula I and
X is
(a) a carboxylic acid group of the formula $R_1-CO-O-$ (IV) or $CF_3-CO-O-$ (V), where $R_1$ in the formula (IV) has the same meaning as in the formula (I),
(b) a carbonic acid group of the formula $R_3-O-CO-O-$ (VI), where $R_3$ is lower alkyl, perfluorinated lower alkyl, unsubstituted aryl or monosubstituted or polysubstituted aryl, wherein the substituent is lower alkyl, lower alkoxy, trifluoromethyl or halogen,
(c) a sulfonic acid group of the formula $R_4-SO_2-O-$ (VII), where $R_4$ is lower alkyl, perfluorinated lower alkyl, unsubstituted aryl or monosubstituted or polysubstituted aryl, wherein the substitutent is lower alkyl, lower alkoxy, trifluoromethyl or halogen, or
(d) a fused or unfused five-membered heterocyclic group having at least two N atoms in the ring, in the presence of an inorganic or organic protonic acid, a Lewis acid or adducts thereof with electron donors in a solvent or solvent mixture inert toward the reactants, at temperatures of $-10°$ C. to the boiling point of the solvent or of the lowest-boiling solvent component, and isolating the resulting compounds of the general formula I from the reacting mixture.

The nomenclature and numbering of positions used in the present description for the glycerophosphocholine and its derivatives follows the rules given in Biochem. J. 171 (1978), 29–35. The abbreviation "sn" in the systematic chemical names of the compounds mentioned denotes "stereospecifically numbered". All position numbers in the present description relating to the position of substituents on the glycerol radical are based on this stereospecific numbering.

$R_1$ and $R_2$ in the meaning of "$C_1$ to $C_{24}$-alkyl" stand in the present description for a straight-chain or single or multiple branched saturated hydrocarbon radical and in the meaning "$C_3$ to $C_{24}$-alkenyl" for a straight-chain or single or multiple branched mono- or polyunsaturated hydrocarbon radical. Both in the meaning "alkyl" and in the meaning "alkenyl", the radicals $R_1$ and $R_2$ can be monosubstituted or polysubstituted, possible substituents for this purpose being preferably halogen atoms, such as chlorine, bromine, iodine or fluorine, or alkoxy radicals, such as methoxy, ethoxy, propyloxy, butyloxy and the like.

The protective triphenylmethyl group of formula II, signified by "T", is preferably unsubstituted. However, to improve the solubility in some cases, it might be advantageous to introduce triphenylmethyl groups which are monosubstituted or polysubstituted on one, two or all three phenyl groups. In this case suitable substituents are particularly straight-chain or branched $C_1$ to $C_6$-alkyl or $C_1$ to $C_6$-alkoxy groups or the abovementioned halogen atoms.

When X in the formula III denotes a carbonic acid radical of the formula VI or a sulfonic acid radical of the formula VII, each of $R_3$ and $R_4$ in these radicals in the meaning "lower alkyl" is preferably a saturated $C_1$ to $C_4$-hydrocarbon radical, such as methyl, ethyl, propyl, isopropyl, butyl, secondary or tertiary butyl, and in the meaning "perfluorinated lower alkyl" one of the abovementioned hydrocarbon radicals where the hydrogen atoms have been replaced by fluorine, preferably trifluoromethyl or perfluoroethyl. In the meaning "unsubstituted or substituted aryl" each of $R_3$ and $R_4$ is preferably an unsubstituted phenyl, 1-naphthyl or 2-naphthyl group or a mono- or polysubstituted phenyl, 1 naphthyl or 2-naphthyl group wherein the substituted is lower alkyl, lower alkoxy, trifluoromethyl or halogen. In the meaning "aralkyl" these radicals preferably stand for a phenyl-substituted lower alkyl radical such as benzyl or phenylehtyl.

Compounds of the general formula III in which X is a five-membered heterocyclic group having at least two N atoms in the ring which may be fused are to be understood as meaning first and foremost the active amides referred to as "carboxylic acid azolides" in the paper by H. A. Staab and W. Rohr "Synthesen mit heterocyclischen Amiden" [Syntheses involving heterocyclic amides] (published in W. Foerst, Neuere Methoden in der präparativen organischen Chemie, V, pages 33 et seq., Georg Thieme Verlag, Stuttgart).

In the present description, these azolides first and foremost include those compounds of the formula $R_1$—CO—X (III) in which $R_1$ has one of the abovementioned meanings and X stands for those heterocyclic radicals which are mentioned in Table I on page 55 of the cited paper of H. A. Staab et al. as heterocyclic radicals by reference to the example of acetic acid azolides.

The reaction of compounds of the formula II with those of the formula III is carried out according to the invention in a polar aprotic solvent or solvent mixture which is inert toward the particular reactants and in which these reactants are readily soluble. They preferably include ethers, such as diethyl ether, diisopropyl ether, tetrahydrofuran, dioxane, ethylene glycol dimethyl ether and the like; halogenated aliphatic and aromatic hydrocarbons, such as methylene chloride, chloroform, 1,2-dichloroethane, carbon tetrachloride, chlorobenzene, p-chlorotoluene and the like; esters, amides and nitriles of carboxylic acids, such as methyl acetate, ethyl acetate, butyl acetate, dimethylformamide, dimethylacetamide, acetonitrile and the like; further hexamethylphosphortriamide, N-methylpyrrolidone, dimethyl sulfoxide or mixtures of the solvents mentioned in any desired composition.

Particularly suitable solvents for the reaction according to the invention are methylene chloride, chloroform, diethyl ether, acetonitrile and ethyl acetate.

Suitable acylating agents of the general formula III for the process according to the invention are again the abovementioned reactive carboxylic acid derivatives. Which is chosen depends in general on the advantages in the preparation and accessibility of these carboxylic acid derivatives as a function of the specific meaning of the radical $R_1$ in the compounds of the formula III. Particularly preferred carboxylic acid derivatives in this respect are anhydrides of the formula III in which X denotes a carboxylic acid radical of the formula IV or mixed anhydrides of the formula III in which X denotes the trifluoroacetate radical of the formula V. Particularly preferred acylating agents further include the "carboxylic acid azolides" of the general formula III in which X denotes the radical of a fused or unfused five-membered heterocycle having at least 2 N atoms in the ring. Examples thereof are the imidazolyl, 1,2,3-triazolyl, 1,2,4-triazolyl, tetrazolyl, benzimidazolyl and benzotriazolyl radicals. Very particular preference is here given in turn to 1-acyl-1,2,4-triazoles and N-acyltetrazoles which are substituted by the particular desired acyl radical $R_1$—CO— which is to be introduced into the position 1 on the glycerol in the course of the reaction according to the invention.

Of the "active ester" acylating agents of the general formula III where X denotes a carbonic acid radical of the formula VI or sulfonic acid radical of the formula VII, very particular preference is given in turn to those compounds where, in the radicals mentioned, $R_3$ has the meaning of methyl, ethyl, benzyl or phenyl and $R_4$ has that of methyl, ethyl or trifluoromethyl.

In the reaction according to the invention, it is surprisingly possible, by means of a completely new piece of process technology, to detach the protective 1-O-trimethylphenyl group in the starting compounds of the general formula II and to introduce the desired acyl radical into the vacated position 1 on the glycerol in a single reaction stage without any isolation of intermediates. Single-stage or single-vessel reactions where two fundamentally different types of reaction, such as the removal of an OH-protecting group to free the hydroxyl function and the acylation thereof, are combined in a single reaction step have hitherto not been disclosed for the preparation of phosphatidylcholines, nor are otherwise known in chemical process technology.

This new piece of process technology occasions the use of a 3-component reaction system which, in addition to the protected starting compounds of the formula II and an acylating agent of the formula III, comprises the presence at the same time of a suitable acidic agent to remove the protective triphenylmethyl group. Suitable acidic agents are on the one hand not only inorganic but also organic protonic acids and on the other Lewis acids. Suitable inorganic protonic acids are preferably liquid or gaseous mineral acids, in this group of acids the passing of dry hydrogen chloride into the reaction mixture having proven of particularly good utility. Of organic protonic acids, preference is given to carboxylic acids and perfluorinated carboxylic acids, very particularly trifluoroacetic acid Or aliphatic and aromatic, facultatively perfluorinated sulfonic acids, such as methanesulfonic acid, ethanesulfonic acid, perfluoromethanesulfonic acid, benzenesulfonic acid, p-toluenesulfonic acid and the like, here in turn preference being given to methanesulfonic acid.

Lewis acids are first and foremost boron trifluoride, boron trichloride, aluminum trichloride, zinc chloride and customarily used adducts thereof with electron donors, such as ethers, mercaptans, thioethers, amines and the like. In the group of Lewis acids, the use of boron trifluoride etherate has proven to be very particularly advantageous.

To practice the single-vessel reaction according to the invention, an advantageous procedure comprises forming a 3-component reaction mixture from the starting compound of the formula II, acylating agent of the formula III and acidic agent in one of the solvents or solvent mixtures mentioned and reacting until conversion is complete.

Basically, the reactants are consumed in mutually equimolar amounts. To raise the reaction rate and improve the yields, however, it has proven advantageous to use not only the acylating agent but also the acidic agent in excess relative to the starting compound of the formula II. In a particularly preferred embodiment of the process, the acylating agent is used in a 1.2 to 2 times molar excess and the acidic agent in a 2 to 8 times molar excess, in each case based on the starting material of the formula II.

The reaction temperature can in principle be freely chosen with a wide range from $-10°$ C. to the boiling point of the solvent or of the lowest-boiling solvent component. Preferably, however, the reaction is carried out within the temperature range from $0°$ C. to $25°$ C.

The reaction time depends on the usual parameters, such as reaction temperature, reactivity of reactants, size of batch and similar factors, and in general ranges from a few minutes to several hours.

The working up of the reaction mixture and isolation of the end products of the general formula I can be carried out using conventional chemical working methods familiar to those skilled in the art. For example, the reaction batch can be neutralized and the 1,2-diacYl-sn-glycero-3-phosphocholines isolated in already a very pure form by partition between two phases and repeated washing of the product-containing phase. Purification of compounds of the formula I is advantageously effected by using chromatographic methods, for example thin layer chromatography, column high pressure liquid chromatography and the like.

The process according to the invention not only makes possible a substantially simpler, less time-consuming and more efficient preparation of mixed-substituted 1,2-diacyl-sn-glycero-3-phosphorcholines but unexpectedly also produces more uniform and purer products than existing processes.

In particular, the isomerization by acyl migration from position 2 to position 1 on the glycerol, which otherwise occurs as an undesirable secondary reaction in most cases, virtually does not occur with the process according to the invention, so that the products obtained are more than 98% pure.

The preparation of the 1-O-triphenylmethyl-2-acyl-sn-glycero-3-phosphocholines used as a starting material in the process according to the invention is described in more detail in U.S. Pat. No. 4.622.180.

The Examples which follow illustrate the invention in more detail:

EXAMPLE 1

1-Palmitoyl-2-oleoyl-sn-glycero-3-phosphocholine 7.63 g (10 mmol) of 1-O-trityl-2-oleoyl-sn-glycero-3-phosphocholine are dissolved in 100 ml of methylene chloride, a solution of 9.90 g (20 mmol) of palmitic anhydride and an ether solution of 5.68 g (40 mmol) of boron trifluoride etherate are added, and the mixture is stirred for one hour at $0°$ C. A 20% strength suspension of 25 g of sodium bicarbonate in water is then added with vigorous stirring which is continued for 10 minutes until the evolution of gas has ended. This is followed by the addition of 50 ml of methanol, filtration, addition of 70 ml of 2/1 chloroform/methanol and phase separation. The bottom phase is washed twice with a weak ammoniacal 1/1 mixture of water/methanol and once with 1/1 water/methanol and then evaporated to dryness.

The oily crude product obtained is purified by chromatography over silica gel. (Eluent: chloroform-methanol-water: 10/20/3, v/v/v). This gives 6.98 g (91.9% of theory) of pure product.

$R_f$=0.40 (CHCl$_3$/CH$_3$OH/conc. NH$_3$=65/35/5, v/v/v) $^1$H-NMR spectrum (delta in ppm):

0.9 (6H, CH$_3$) 1.3 (CH$_2$) 1.6–2.3 (alpha- and beta-CH$_2$) 3.16 (9H, s, N-CH$_3$) 3.3–4.4 (8H, CH$_2$, glycerol, choline) 5.1 (1H, CH-glycerol) 5.34 (2H, olefin)

Elemental analysis: C$_{42}$H$_{82}$NO$_8$P (MW=760.09) calculated: C 66.37, H 10.87, N 1.84, P 4.08, found: C66.2, H 10.9, N 1.7, N 3.9.

The working method of Example 1 was repeated to obtain:

EXAMPLE 2

1-Palmitoyl-2-oleoyl-sn-glycero-3-phosphocholine by reaction of 7.63 g (10 mmol) of 1-O-trityl-2-oleoyl-sn-glycero-3-phosphocholine with 5.86 g (20 mmol) of 1-palmitoyl-1,2,4-triazole in the presence of 11.36 g (80 mmol) of boron trifluoride etherate.

Yield: 6.84 g (90% of theory) of pure product, which is identical to that obtained in Example 1.
Preparation of 1-palmitoyl-1,2,4-triazole:

Palmitoyl chloride is dissolved in methylene chloride and added dropwise to a solution of 2 equivalents of 1,2,4-triazole in methylene chloride, the mixture is stirred for some hours at room temperature and filtered, and the filtrate is used directly in the reaction.

EXAMPLE 3

1-Palmitoyl-2-oleoyl-sn-glycero-3-phosphocholine by reaction of 763 mg (1 mmol) of 1-O-trityl-2-oleoyl-sn-glycero-3-phosphocholine with 628 mg (2 mmol) of palmitoyl ethyl carbonate in the presence of 568 mg (4mmol) of boron trifluoride etherate at $20°$ C.

Yield: 614 mg (80.8 % of theory) of pure product, which is identical with that obtained in Example 1.
Preparation of palmitoyl ethyl carbonate:

Palmitic acid and ethyl chloroformate are reacted with methylene chloride in a molar ratio of 1:1 in the presence of dry sodium carbonate. Inorganic material is filtered off, and the resulting filtrate is used directly in the reaction.

EXAMPLE 4

1-Palmitoyl-2-oleoyl-sn-glycero-3-phosphocholine by reaction of 7.63 g (10 mmol) of 1-O-trityl-2-oleoyl-sn-glycero-3-phosphocholine, dissolved in 100 ml of anhydrous diethyl ether, with 9.90 g (20 mmol) of palmitic anhydride and 5.68 g (40 mmol) of boron trifluoride etherate at $20°$ C.

Yield: 4.53 g (59.6% of theory) of pure product, identical to that of Example 1.

EXAMPLE 5

1-Palmitoyl-2-oleoyl-sn-glycero-3-phosphocholine by reaction of 3.82 g (5 mmol) of 1-O-trityl-2-oleoyl-sn-glycero-3-phosphocholine, dissolved in 50 ml of anhydrous acetonitrile, with 4.95 g (10 mmol) of palmitic anhydride and 2.84 g (20 mmol) of boron trifluoride etherate at 20° C.

Yield: 2.19 g (57.6% of theory) of pure product, identical to that of Example 1.

EXAMPLE 6

1-Palmitoyl-2-oleoyl-sn-glycero-3-phosphocholine by reaction of 3.82 g (5 mmol) of 1-O-trityl-2-oleoyl-sn-glycero-3-phosphocholine, dissolved in 50 ml of anhydrous carbon tetrachloride, with 4.95 g (10 mmol) of palmitic anhydride and 2.84 g (20 mmol) of boron trifluoride etherate at 20° C.

Yield: 2.84 g (74.7% of theory) of pure product, identical to that of Example 1.

EXAMPLE 7

1-Stearoyl-2-palmitoyl-sn-glycero-3-phosphocholine by reaction of 1.48 g (2 mmol) of 1-O-trityl-2-palmitoyl-sn-glycero-3-phosphocholine with 2.20 g (4 mmol) of stearic anhydride in the presence of 1.14 g (8 mmol) of boron trifluoride etherate.

Yield: 1.35 g (88.3% of theory) of pure product.

$R_f$=0.40 (mobile phase as in Example 1)

NMR: 0.9 (6H, CH$_3$) 1.3 (CH$_2$) 1.6–2.3 (alpha- and beta-CH$_2$) 3.16 (9H, s, N—CH$_3$) 3.3–4.4 (8H, CH$_2$, glycerol, choline) 5.12 (1H, CH-glycerol).

Elemental analysis: $C_{42}H_{84}NO_8P$ (MW=762.11). calculated: C 66.19, H 11.11, N 1.84, P 4.06, found: C 65.9, H 11.4, N 1.7, P 3.9.

EXAMPLE 8

1-Palmitoyl-2-acetyl-sn-glycero-3-phosphocholine by reaction of 1.08 g (2 mmol) of 1-O-trityl-2-acetyl-sn-glycero-3-phosphocholine with 1.98 g (4 mmol) of palmitic anhydride and 1.14 g (8 mmol) of boron trifluoride etherate.

Yield: 0.94 g (87.4% of theory) of pure product.

$R_f$=0.28 (mobile phase as Example 1).

NMR: 0.9 (3H, CH$_3$) 1.3 (CH$_2$) 1.6–2.3 (alpha- and beta-CH$_2$) 2.13 (3H, s, CH$_3$CO) 3.16 (9H, s, N—CH$_3$) 3.3–4.4 (8H, CH$_2$—glycerol, choline) 5.1 (1H, CH-glycerol).

Elemental analysis: $C_{26}H_{52}NO_8P$ (MW=537.67). calculated: C 58.08, H 9.75, N 2.60, P 5.76, found: C 57.8, H 10.1, N 2.4, P 5.5.

EXAMPLE 9

1-Stearoyl-2-methoxyacetyl-sn-glycero-3-phosphocholine by reaction of 572 mg (1 mmol) of 1-O-trityl-2-methoxyacetyl-sn-glycero-3-phosphocholine with 1.10 g (2 mmol) of stearic anhydride and 568 mg (4 mmol) of boron trifluoride etherate.

Yield: 522 mg (87.6% of theory) of pure product $R_f$=0.27 (mobile phase as Example 1)

NMR: 0.9 (3H, CH$_3$) 1.3 (CH$_2$) 1.6–2.3 (alpha- and beta-CH$_2$) 3.16 (9H, s, N—CH$_3$) 3.52 (3H, S, CH$_3$O) 3.3–4.4 (8H, CH$_2$, glycerol, choline) 5.1 (1H, CH-glycerol) 5.25 (2H, s, O—CH$_2$—O).

Elemental analysis: $C_{29}H_{58}NO_9P$ (MW=595.750). calculated: C 58.47, H 9.81, N 2.35, P 5.20, found: C 58.2, H 10.0, N 2.2, P 5.0.

EXAMPLE 10

1-Oleoyl-2-(2-ethylhexanoyl)-sn-glycero-3-phosphocholine by reaction of 1.79 g (3 mmol) of 1-O-trityl-2-(2-ethylhexanoyl)-sn-glycero-3-phosphocholine and 3.28 g (6 mmol) of oleic anhydride and 1.70 g (12 mmol) of boron trifluoride etherate.

Yield: 1.72 g (88.5% of theory) of pure product.

$R_f$=0.40 (mobile phase as Example 1).

NMR: 0.9 (9H, CH$_2$) 1.3 (CH$_2$) 1.6–2.5 (alpha- and beta-CH$_2$) 3.16 (9H, s, N—CH$_3$) 3.3–4.4 (9H, CH$_2$, glycerol, choline, CHCO) 5.1 (1H, CH-glycerol) 5.34 (2H, olefin).

Elemental analysis: $C_{34}H_{66}NO_8P$ (MW=647.874). calculated: C 63.03, H 10.27, N 2.16, P 4.78, found: C 63.2, H 10.1, N 2.2, P 4.9.

EXAMPLE 11

1-Stearoyl-2-(9,10-dibromostearoyl)-sn-glycero-3-phosphocholine by reaction of 924 ml (1 mmol) of 1-O-trityl-2-(9.10-dibromostearoyl)-sn-glycero-phosphocholine with 1.10 g (2 mmol) of stearic anhydride and 568 mg (4 mmol) of boron trifluoride etherate.

Yield: 866 mg (91.4% of theory) of pure product.

$R_f$=0.40 (mobile phase as Example 1).

NMR: 0.9 (6H, CH$_3$) 1.3 (CH$_2$) 1.6–2.5 (alpha and beta-CH$_2$) 3.16 (9H, s, N-CH$_3$) 3.3–4.4 (8H, CH$_2$, glycerol, choline) 5.1 (3H, n, CH-glycerol, CH-Br).

Elemental analysis: $C_{44}H_{86}Br_2NO_8P$ (MW=947.969). calculated: C 55.75, H 9.14, N 1.48, P 3.27, Br 16.86, found: C 55.5, H 9.4, N 1.3, P 3.0, Br 16.4.

EXAMPLE 12

1-Oleoyl-2-tetracosanoyl-sn-glycero-3-phosphocholine by reaction of 850 mg (1 mmol) 1-O-trityl-2-tetracosanoyl-sn-glycero-3-phosphocholine with 833 mg (2 mmol) of oleoyl benzyl carbonate and 568 mg (4 mmol) of boron trifluoride etherate at 20° C.

Yield: 472 mg (54.1% of theory) of pure product.

$R_f$=0.42 (mobile phase as Example 1).

NMR: 0.9 (6H, CH$_3$) 1.3 (CH$_2$) 1.6–2.3 (alpha- and beta-CH$_2$) 3.16 (9H, s, N—CH$_3$) 3.3–4.4 (8H, glycerol, choline) 5.1 (1H, CH-glycerol) 5.36 (2H olefin).

Elemental analysis: $C_{50}H_{98}NO_8P$ (MW=872.311) calculated: C 68.85, H 11.32, N 1.61, P 3.55, found: C86.5, H 11.5, N 1.4, P 3.4.

Preparation of oleoyl benzyl carbonate:

Example 3 is repeated to react oleic acid with benzyl chloroformate in the presence of dry sodium carbonate.

EXAMPLE 13

1-Palmitoyl-2-propionyl-sn-glycero-3-phosphocholine by reaction of 1.12 g (2 mmol) of 1-O-trityl-2-propionyl-sn-glycero-3-phosphocholine with 1.41 g (4 mmol) of trifluoroacetyl palmitate and 1.14 g (8 mmol) of boron trifluoride etherate at 20° C.

Yield: 786 mg (71.2% of theory) of pure product.

$R_f$=0.29 (mobile phase as Example 1).

NMR: 0.9 (3H, CH$_3$) 1.3 (CH$_2$) 1.6–2.3 (alpha- and beta-CH$_2$, beta-CH$_3$) 3.16 (9H, s, N—CH$_3$) 3.2–4.4 (8H, m, CH$_2$ glycerol, choline) 5.12 (1H-CH-glycerol).

Elemental analysis: $C_{27}H_{54}NO_8P$ (MW=551.70) calculated: C 58.78, H 9.87, N 2.54, P 5.61, found: C 58.6, H 10.0, N 2.4, P 5.5.

Preparation of trifluoroacetyl palmitate:

Example 2 is repeated to react palmitic acid with trifluoroacetic anhydride.

EXAMPLE 14

1-Palmitoyl-2-butyryl-sn-glycero-3-phosphocholine by reaction of 1.14 g (2 mmol) of 1-O-trityl-2-butyryl-sn-glycero-phosphocholine with 3.08 g (4 mmol) of N-palmitoyltetrazole and 5.68 g (8 mmol) of boron trifluoride etherate.

Yield: 1.09 g (96.3% of theory) of pure product.
$R_f = 0.31$ (mobile phase as Example 1).
NMR: 0.9 (6H, $CH_3$) 1.3 ($CH_2$) 1.6–2.3 (alpha- and beta-$CH_2$) 3.15 (9H, s, N—$CH_3$) 3.1–4.3 (8H, m $CH_2$ glycerol, choline) 5.13 (1H CH-glycerol).
Elemental analysis: $C_{28}H_{56}NO_8P$ (MW=565.73) calculated: C 59.45, H 9.98, N 2.48, P 5.47, found: C 59.4, H 10.2, N 2.4, P 5.3.

Preparation of N-palmitoyltetrazole:
Example 2 is repeated to react palmitoyl chloride with tetrazole in a molar ratio of 1:2.

EXAMPLE 15

1-Oleoyl-2-isobutyryl-sn-glycero-3-phosphocholine by reaction of 1.14 g (2 mmol) of 1-O-trityl-2-isobutyryl-sn-glycero-3-phosphocholine with 2.19 g (4 mmol) of oleic anhydride and 5.68 g (8 mmol) of boron trifluoride etherate.

Yield: 1.09 g (92.1% of theory) of pure product.
$R_f = 0.31$ (mobile phase as Example 1)
NMR: 0.9 (3H, $CH_3$) 1.3 ($CH_2$) 1.6–2.3 (alpha- and beta-$CH_2$, beta-$CH_3$) 3.14 (9H, s, N—$CH_3$) 3.1–4.3 (9H, $CH_2$, glycerol, choline, CH-CO), 5.12 (1H CH-glycerol) 5.36 (2H, m, olefin).
Elemental analysis: $C_{30}H_{58}NO_8P$ (MW=591.78) calculated: C 60.89, H 9.91, N 2.37, P 5.23, found: C 60.7, H 10.1, N 2.4, P 5.1.

EXAMPLE 16

1-Stearoyl-2-linoleoyl-sn-glycero-3-phosphocholine by reaction of 3.81 g (5 mmol) of 1-O-trityl-2-linoleoyl-sn-glycero-3-phosphocholine with 3.36 g (10 mmol) of 1-stearoyl-1,2,4-triazole and 5.68 g (40 mmol) of boron trifluoride etherate under argon.

Yield: 3.32 (84.5% of theory).
NMR: 0.9 (6H, $CH_3$) 1.3 ($CH_2$) 1.6–2.3 (alpha- and beta-$CH_2$) 2.75 (2H, =C—$CH_2$—C=) 3.16 (9H, s, N—$CH_3$) 3.3–4.4 (8H, $CH_2$ glycerol, choline) 5.1 (1H, CH-glycerol), 5.35 (4H, m, olefin).
Elemental analysis: $C_{44}H_{84}NO_8P$ (MW=786.131). calculated: C 67.23, H 10.77, N 1.78, P 3.94, found: C 67.0, H 10.9, N 1.7, P 3.7.

Preparation of 1-stearoyl-1,2,4-triazole:
Similar to the preparation of 1-palmitoyl-1,2,4-triazole in Example 2.

EXAMPLE 17

1-($^{14}$C)Oleoyl-2-($^3$H)oleoyl-sn-glycero-3-phosphocholine by reaction of 381 mg (0.5 mmol) of 1-O-trityl-2-($^3$H)-oleoyl-sn-glycero-3-phosphocholine ($1.2 \times 10^8$ cpm/mmol), dissolved in 5 ml of methylene chloride, with 334 mg (1 mmol) of ($^{14}$C)-1-oleoyl-1,2,4-triazole ($1.9 \times 10^6$ cpm/mmol) and 568 mg (4 mmol) of boron trifluoride etherate at 20° C.

Yield: 354 mg (90% of theory) of pure product.
$R_f = 0.42$ ($CHCl_3/CH_3OH$/conc. $NH_3$ 65/35/5, v/v/v).
NMR: 0.88 (6H, $CH_3$), 1.26 ($CH_2$), 1.6–2.3 (—$CH_2$—CH=CH, (—$CH_2$—$CH_2$—C=O) 3.16 (9H, s, N—$CH_3$) 3.3–4.4 (8H, $CH_2$, glycerol, choline) 5.1 (1H, glycerol).

Specific activity:
$^3$H: $1.18 \times 10^8$ cpm/mmol,
$^{14}$C: $0.9 \times 10^6$ cpm/mmol.

Preparation of 1-($^{14}$C)-oleoyl-1,2,4-triazole:
The substance is prepared similarly to Example 2.

EXAMPLE 18

1-($^{14}$C)Oleoyl-2-($^3$H)oleoyl-sn-glycero-3-phosphocholine by reaction of 381 mg (0.5 mmol) of 1-O-trityl-2-($^3$H)-oleoyl-sn-glycero-3-phosphocholine ($1.2 \times 10^8$ cpm/mmol), dissolved in 5 ml of methylene chloride, with 547 mg (1 mmol) of ($^{14}$C)oleic anhydride ($3.8 \times 10^6$ cpm/mmol) and 284 mg (2 mmol) of boron trifluoride etherate at 0° C.

Yield: 342 mg (86.9% of theory) of pure product, which is identical to that obtained in Example 17.

EXAMPLE 19

1-Stearoyl-2-arachidonoyl-sn-glycerol-3-phosphocholine by reaction of 384 mg (0.5 mmol) of 1-O-trityl-2-arachidonoyl-sn-glycero-3-phosphocholine with 335 mg (1 mmol) of 1-stearoyl-1,2,4-triazole and 568 mg (4 mmol) of boron trifluoride etherate under argon.

Yield: 372 mg (91.8% of theory) of pure product.
$R_f = 0.38$ (mobile phase as Example 1).
NMR: 0.9 (6H, $CH_3$) 1.3 ($CH_2$); 1.6–2.3 (alpha- and beta-$CH_2$) 2.8 (6H, =C—$CH_2$—C=) 3.16 (9H, s, N—$CH_3$) 3.3–4.4 (8H, $CH_2$, glycerol, choline) 5.1 (1H, CH-glycerol) 5.35 (8H, olefin).
Elemental analysis: $C_{46}H_{84}NO_8P$ (MW=810.151). calculated: C 68.20, H 10.45, N 1.73, P 3.82, found: C 68.0, H 10.7, N 1.6, P 3.7.

EXAMPLE 20

1-Palmitoyl-2-(3-trifluoromethylbutyryl)-sn-glycero-3-phosphocholine by reaction of 638 mg (1 mmol) of 1-O-trityl-2-(3-trifluoromethylbutyryl)-sn-glycero-3-phosphocholine and 586 mg (2mol) of 1-palmitoyl-1,2,4-triazole and 1.14 g (8 mmol) of boron trifluoride etherate.

Yield: 571 mg (90.4% of theory) of pure product.
$R_f = 0.32$ (mobile phase as Example 1).
NMR: 0.9 (3H, $CH_3$) 1.3 ($CH_2$) 1.6–2.5 (alpha- and beta-$CH_2$, gamma-$CH_3$) 3.16 (9H, s, N-$CH_3$) 3.1–4.5 (9H, $CH_2$, glycerol, choline, CH-$CF_3$), 5.13 (1 H, CH-glycerol).
Elemental analysis: $C_{29}H_{53}F_3NO_8P$ (MW=631.717) calculated: C 55.14, H 8.46, N 2.18, P 4.90, F 9.02, found: C 55.0, H 8.7, N 2.0, P 4.8, F 8.8.

EXAMPLE 21

1-Palmitoyl-2-(2-butylhexanoyl)-sn-glycero-3-phosphocholine by reaction of 1.31 g (2 mmol) of 1-O-trityl-2-(2-butylhexanoyl)-sn-glycero-3-phosphocholine with 1.17 g (4 mmol) of 1-palmitoyl-1,2,4-triazole and 2.28 g (16 mmol) of boron trifluoride etherate.

Yield: 1.17 g (90.0% of theory) of pure product.
$R_f = 0.36$ (mobile phase as Example 1).
NMR: 0.9 (9H, $CH_3$) 1.3 ($CH_2$) 1.6–2.3 (alpha- and beta-$CH_2$) 3.15 (9H, s, N-$CH_3$) 3.1–3.4 (9H, $CH_2$, glycerol, choline, CH-CO) 5.1 (1H, CH-glycerol).
Elemental analysis: $C_{34}H_{68}NO_8P$ (MW=649.89) calculated: C 62.84, H 10.55, N 2.16, P 4.77, found: C 62.7, H 10.7, N 2.1, P 4.5.

EXAMPLE 22

1-Palmitoyl-2-oleoyl-sn-glycero-3-phosphocholine by reaction of 1.53 g (2 mmol) of 1-O-trityl-2-oleoyl-snglycero-3-phosphocholine, dissolved in 20 ml of anhydrous methylene chloride, with 1.98 g (4 mmol) of palmitic anhydride and 1.09 g (8 mmol) of zinc chloride during eight hours at 20° C.

Yield: 1.21 g (80% of theory) of pure product, identical to that of Example 1.

EXAMPLE 23

1-Palmitoyl-2-oleoyl-sn-glycero-3-phosphocholine by reaction of 763 mg (1 mmol) of 1-O-trityl-2-oleoyl-sn-glycero-3-phosphocholine with 990 mg (2 mmol) of palmitic anhydride in 50 ml of anhydrous methylene chloride by passing in HCl gas in the absence of moisture to saturation at room temperature in the curse of one hour.

Yield: 379 mg (49.8% of theory) of pure product, identical to that of Example 1.

EXAMPLE 24

1-Palmitoyl-2-oleoyl-sn-glycero-3-phosphocholine by reaction of 1.53 g (2 mmol) of 1-O-trityl-2-oleoyl-sn-glycero-3-phosphocholine, dissolved in 20 ml of anhydrous methylene chloride, with 1.98 g (4 mmol) of palmitic anhydride and 1.82 g (16 mmol) of trifluoroacetic acid in the course of one hour at 20° C.

Yield: 0.91 g (59.8% of theory) of pure product, identical to that of Example 1.

EXAMPLE 25

1-Palmitoyl-2-oleoyl-sn-glycero-3-phosphocholine by reaction of 763 mg (1 mmol) of 1-O-trityl-2-oleoyl-sn-glycero-3-phosphocholine with 990 mg (4 mmol) of palmitic anhydride and 532 mg (4 mmol) of aluminum chloride, dissolved in 1 ml of ether, during one hour at 20° C.

Yield: 304 mg (40.0% of theory) of pure product, identical with that of Example 1.

EXAMPLE 26

1-Acetyl-2-palmitoyl-sn-glycero-3-phosphocholine by reaction of 7.68 g (10 mmol) of 1-O-(4-methoxytriphenyl)-2-palmitoyl-sn-glycero-3-phosphocholine with 2.04 g (20 mmol) of acetic anhydride and 5.68 g (40 mmol) of boron trifluoride etherate.

Yield: 4.87 g (90.6% of theory) of pure product.
$R_f=0.28$ (mobile phase as Example 1)
NMR: 0.9 (3H, CH$_3$) 1.3 (CH$_2$) 1.6–2.3 (alpha- and beta-CH$_2$) 2.11 (3H, s, CH$_3$CO) 3.14 (9H, s, H-CH$_3$) 3.3–4.4 (8H, CH$_2$ -glycerol, choline) 5.11 (1H, CH-glycerol).
Elemental analysis: $C_{26}H_{52}NO_8P$ (MW=537.67). calculated: C 58.08, H 9.75, N 2.60, P 5.76, found: C 58.0, H 9.9, N 2.5, P 5.6.

EXAMPLE 27

1(2-Ethylhexanoyl)-2-palmitoyl-sn-glycero-3-phosphcholine. by reaction of 1.60 g (2 mmol) of 1-(4,4'-dimethoxytriphenylmethyl)-2-palmitoyl-sn-glycero-3-phosphocholine with 1.04 g (4 mmol) of 2-ethylhexanoic anhydride and 1.14 g (8 mmol) of boron trifluoride etherate.

Yield: 1.10 g (88.4% of theory) of pure product.
$R_f=0.38$ (mobile phase as Example 1).
NMR: 0.9 (9H, CH$_3$) 1.3 (CH$_2$) 1.6–2.5 (alpha- and beta CH$_2$) 3.15 (9H, s, N—CH$_3$), 3.3–4.4 (9H, CH$_2$, glycerol, choline, CH—CO); 5.12 (1H, CH-glycerol).

Elemental analysis: $C_{32}H_{64}NO_8P$ (MW=621.83). calculated: C 61.81, H 10.37, N 2.25, P 4.98, found: C 61.7, H 10.4, N 2.1, P 4.8.

EXAMPLE 28

1-(9,10-Dibromostearoyl)-2-palmitoyl-sn-glycero-3-phosphocholine by reaction of 409 mg (0.5 mmol) of 1-O-(4,4', 4''-trimethoxytriphenylmethyl)-2-palmitoyl-sn-glycero-3-phosphocholine with 867 mg (1 mmol) of 9.10, -dibromostearic anhydride and 284 mg (2 mmol) of boron trifluoride etherate.

Yield: 411 mg (89.3% of theory) of pure product.
$R_f=0.40$ (mobile phase as Example 1).
NMR: 0.9 (6H, CH$_3$) 1.3 (CH$_2$) 1.6–2.5 (alpha- and beta-CH$_2$) 3.14 (9H, s, N—CH$_3$) 3.3–4.4 (8H, CH$_2$ glycerol, choline) 5.15 (3H, m, CH-glycerol, CH-Br).
Elemental analysis: $C_{42}H_{82}Br_2NO_8P$ (MW=919.915). calculated: C 54.84, H 8.98, N 1.52, P 3.37, found: C 54.6, H 10.1, N 1.4, P 3.4.

EXAMPLE 29

1-Tetracosanoyl-2-palmitoyl-sn-glycero-3-phosphocholine by reaction of 752 mg (1 mmol) of 1-O-(4-methyltriphenylmethyl)-2-palmitoyl-sn-glycerol-3-phosphocholine with 1.44 g (2 mmol) of tetracosanoic anhydride and 568 mg (4 mmol) of boron trifluoride etherate at 20° C.

Yield: 758 mg (89.6% of theory) of pure product.
$R_f=0.42$ (mobile phase as Example 1).
NMR: 0.9 (6H, CH$_3$) 1.3 (CH$_2$) 1.6–2.3 (alpha- and beta-CH$_2$) 3.15 (9H, s, N—CH$_3$) 3.3–4.4 (8H, glycerol, choline) 5.11 (1H, CH-glycerol).
Elemental analysis: $C_{48}H_{96}NO_8P$ (MW=846.272), calculated: C 68.13, H 11.43, N 1.66, P 3.66, found: C 68.3, H 11.6, N 1.6, P 3.4.

EXAMPLE 30

1-linoleoyl-2-palmitoyl-sn-glycero-3-phosphocholine by reaction of 1.64 g (2 mmol) of 1-O-(4-n-heyxyltriphenylmethyl)-2-palmitoyl-sn-glycero-3-phosphocholine with 2.33 g (4 mmol) of linoleic anhydride and 1.14 g (8 mmol) of boron trifluoride etherate at 20° C. under argon.

Yield: 11 g (93.0% of theory) of pure product.
$R_f=0.40$ (mobile phase as Example 1).
NMR: 0.9 (6H, CH$_3$) 1.3 (CH$_2$) 1.5–2.3 (alpha- and beta-CH$_2$) 2.75 (2H, m, =C—CH$_2$—C=) 3.14 (9H, s, N—CH$_3$) 3.3–4.4 (8H, CH$_2$ glycerol, choline) 5.11 (1H, CH-glycerol) 5.35 (4H, m, olefin).
Elemental analysis: $C_{42}H_{80}NO_8P$ (MW=758.082) calculated: C 66.55, H 10.64, N 1.85, P 4.09, found: C 66.2, H 10.9, N 1.7, P 3.8.

EXAMPLE 31

1-(3-Trifluoromethylbutyryl)-2-palmitoyl-sn-glycero-3-phosphocholine by reaction of 780 mg (1 mmol) of 1-O-(4-isopropyltriphenylmethyl)-2-palmitoyl-sn-glycero-3-phosphocholine with 588 mg (2 mmol) of 3-trifluoromethylbutyric anhydride and 568 mg (4 mmol) of boron trifluoride etherate at 20° C.

Yield: 567 mg (89.8% of theory) of pure product.
$R_f=0.31$ (mobile phase as Example 1).
NMR: 0.9 (3H, CH$_3$) 1.3 (CH$_2$) 1.5–2.5 (alpha- and beta-CH$_2$, gamma-CH$_3$) 3.15 (9H, s, N—CH$_3$) 3.1–4.5 (9H, CH$_2$, glycerol, choline, CH-CF$_3$), 5.1 (1H, CH-glycerol).

Elemental analysis: $C_{29}H_{53}F_3NO_8P$ (MW=631.717) calculated: C 55.14, H 8.46, N 2.18, P 4.90, F 9.02, found: C 54.9, H 8.7, N 2.0, P 4.7, F 8.9.

EXAMPLE 32

1-Butyryl-2-palmitoyl-sn-glycero-3-phosphocholine by reaction of 2.51 g (3 mmol) of 1-O-(4-n-hexyloxytriphenylmethyl)-2-palmitoyl-sn-glycero-3-phosphocholine with 0.95 g (6 mmol) of butyric anhydride and 1.70 g (12 mmol) of boron trifluoride etherate.

Yield: 1.52 g (89.6% of theory) of pure product.

$R_f = 0.30$ (mobile phase as Example 1).

NMR: 0.9 (6H, $CH_3$) 1.3 ($CH_2$) 1.6–2.3 (alpha- and beta-$CH_2$) 3.16 (9H, s, N-$CH_3$); 3.1–4.3 (8H, m, $CH_2$ glycerol, choline), 5.11 (1H, CH-glycerol).

Elemental analysis: $C_{28}H_{56}NO_8P$ (MW=565.73) calculated: C 59.45, H 9.98, N 2.48, P 5.47, found: C 59.2, H 10.2, N 2.2, P 5.3.

EXAMPLE 33

1-Palmitoyl-2-oleoyl-sn-glycero-3-phosphocholine by reaction of 1.68 g (2 mmol) of 1-O-(4-bromotriphenylmethyl)-2-oleoyl-sn-glycero-3-phosphocholine with 1.98 g (4 mmol) of palmitic anhydride and 1.14 g (8 mmol) of boron trifluoride etherate of 20° C.

Yield: 940 mg (61.8% of theory) of pure product, identical to that of Example 1.

EXAMPLE 34

1-Palmitoyl-2-oleoyl-sn-glycero-3-phosphocholine by reaction of 41.4 mg (0.5 mmol) of 1-O-(5-chloro-2-methoxytriphenylmethyl)-2-oleoyl-sn-glycero-3-phosphocholine with 495 mg (1.0 mmol) of palmitic anhydride and 284 mg (2.0 mmol) of boron trifluoride etherate at 20° C.

Yield: 283 mg (74.5% of theory) of pure product, identical to that of Example 1.

EXAMPLE 35

1-Palmitoyl-2-oleoyl-sn-glycero-3-phosphocholine by reaction of 436 mg (0.5 mmol) of 1-O-(3-bromo-4-methoxytriphenylmethyl)-2-oleoyl-sn-glycero-3-phosphocholine with 495 mg (1 mmol) of palmitic anhydride and 284 mg (2 mmol) of boron trifluoride etherate at 20° C.

Yield: 300 mg (78.9% of theory) of pure product, identical to that of Example 1.

EXAMPLE 36

1-Palmitoyl-2-oleoyl-sn-glycerol-3-phosphocholine by reaction of 798 mg (1 mmol) of 1-O-(2-chlorotriphenylmethyl)-2-oleoyl-sn-glycero-3-phosphocholine with 990 mg (2 mmol) of palmitic anhydride and 568 mg (4 mmol) of boron trifluoride etherate at 20° C.

Yield: 453 mg (59.6% of theory) of pure product, identical to that of Example 1.

EXAMPLE 37

1-Palmitoyl-2-oleoyl-sn-glycero-3-phosphocholine by reaction of 411 mg (0.5 mmol) of 1-O-(4-isopropoxytriphenylmethyl)-2-oleoyl-sn-glycero-3-phosphocholine with 495 mg (1 mmol) of palmitic anhydride and 284 mg (2 mmol) of boron trifluoride etherate at 20° C.

Yield: 338 mg (88.9% of theory) of pure product, identical to that of Example 1.

What we claim is:

1. A single-stage process for preparing mixed substituted enantiomerically pure 1,2-diacyl-sn-glycero-3-phosphocholines of the general formula:

$$\begin{array}{c} \quad\quad\quad\quad H_2C-O-\overset{O}{\underset{\|}{C}}-R_1 \\ R_2-\overset{O}{\underset{\|}{C}}-O-CH \quad\quad O^- \quad\quad CH_3 \\ \quad\quad\quad\quad H_2C-O-\overset{\|}{\underset{O}{P}}-O-CH_2-CH_2-\overset{+}{\underset{CH_3}{N}}-CH_3 \end{array} \quad \text{I}$$

in which each of $R_1$ and $R_2$ is different and independently of each other is a straight-chain or single or multiple branched unsubstituted $C_1$ to $C_{24}$-alkyl or mono- or polyunsaturated $C_3$ to $C_{24}$-alkenyl group or a straight-chain or single or multiple branched monosubstituted or polysubstituted $C_1$ to $C_{24}$-alkyl or mono- or polyunsaturated $C_3$ to $C_{24}$-alkenyl group, wherein the substituent is chlorine, bromine, iodine, fluorine or a $C_1$ to $C_{24}$ alkoxy group, which comprises reacting a 1O-triphenyl-2-acyl-sn-glycero-3-phosphocholine of the general formula:

$$\begin{array}{c} \quad\quad\quad\quad H_2C-O-T \\ R_2-\overset{O}{\underset{\|}{C}}-O-CH \quad\quad O^- \quad\quad CH_3 \\ \quad\quad\quad\quad H_2C-O-\overset{\|}{\underset{O}{P}}-O-CH_2-CH_2-\overset{+}{\underset{CH_3}{N}}-CH_3 \end{array} \quad \text{II}$$

in which $R_2$ is as defined in formula I and T is an unsubstituted triphenylmethyl group or a triphenylmethyl group which is monosubstituted or polysubstituted on one, two or all three phenyl groups, wherein each substituent is a straight-chain or branched $C_1$ to $C_6$-alkyl or $C_1$ to $C_6$-alkoxy group or cholrine, bromine, iodine or fluorine with a reactive carboxylic acid derivative of the general formula:

$$R_1-CO-X \quad \text{III}$$

in which $R_1$ is as defined in formula I and X is
(a) a carboxylic acid group of the formula $R_1CO-O-$(IV) or $CF_3-CO-O-$(V), where $R_1$ in formula (IV) has the same meaning as in formula (I);
(b) a carbonic acid group of the formula $R_3-O-CO-O-$(VI), where $R_3$ is lower alkyl, perfluorinated lower alkyl, unsubstituted aryl or monosubstituted or polysubstituted aryl, wherein the substituent is lower alkyl, lower alkoxy, trifluoromethyl or halogen;
(c) a sulfonic acid group of the formula $R_4-SO_2-$(VII), where $R_4$ is lower alkyl, perfluorinated lower alkyl, unsubstituted aryl or monosubstituted or polysubstituted aryl, wherein the substituent is lower alkyl, lower alkoxy, trifluoromethyl or halogen; or
(d) a fused or unfused five-membered heterocyclic group having at least two nitrogen atoms in the ring;

in the presence of an inorganic or organic protonic acid, a Lewis acid or adducts thereof with electron donors in a solvent or solvent mixture inert toward the reactants, at a temperature within the range of $-10°$ C. to the boiling point of the solvent or of the lowest-boiling solvent component, and isolating the resulting compounds of general formula I from the reaction mixture.

2. The process as claimed in claim 1, in which the solvent is methylene chloride, chloroform, diethyl ether, acetonitrile or ethyl acetate.

3. The process as claimed in claim 1, in which the reactive carboxylic acid derivative is an anhydride of the formulal III, in which X denotes a carboxylic acid group of the formula IV or a mixed anhydride of the formula III in which X denotes the trifluoroacetate group of the formula V.

4. The process as claimed in claim 1, in which the reactive carboxylic acid derivative of the formula III is acyl-1,2,4-triazole or N-acyltetrazole, acyl denoting a group $R_1$—CO— where $R_1$ is as defined in claim 1.

5. The process as claimed in claim 1 in which the reactive carboxylic acid derivative is a compound of the formula III in which X represents a carbonic acid group of the formula VI or a sulfonic acid group of the formula VII and in these radicals $R_3$ denotes methyl, ethyl, benzyl or phenyl and $R_4$ denotes methyl, ethyl or trifluoromethyl.

6. The process as claimed in claim 1, in which the reaction is carried out in the presence of dry, gaseous HCl as the inorganic protonic acid, or of trifluoroacetic acid or of methanesulfonic acid as the oganic protonic acid.

7. The process as claimed in claim 1, in which the reaction is carried out in the presence of boron trifluoride, boron trichloride, aluminum trichloride or zinc chloride as the Lewis acid.

8. The process as claimed in claim 1, in which the reaction is carried out in the presence of boron trifluoride etherate as the Lewis acid adduct with electron donors.

9. The process as claimed in claim 1 in which the reaction is carried out in the temperature range between 0° and 25° C.

10. The process as claimed in claim 1, in which there is used, per mole of the starting compound of formula II, 1.2 to 2 moles of the reactive carboxylic acid derivative of formula III and 2 to 8 moles of the inorganic or organic protonic acid, Lewis acid or adducts thereof with electron donors.

* * * * *